United States Patent
Hatakeyama et al.

(10) Patent No.: US 7,465,579 B2
(45) Date of Patent: Dec. 16, 2008

(54) DEVICE AND METHOD FOR INTRODUCING PARTICLE INTO CELL AND DEVICE AND METHOD FOR COLLECTING PARTICLE FROM CELL

(75) Inventors: Satoru Hatakeyama, Kawasaki (JP);
Hideaki Okamoto, Yokohama (JP);
Norihiko Utsunomiya, Machida (JP);
Junta Yamamichi, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 411 days.

(21) Appl. No.: 11/165,524

(22) Filed: Jun. 24, 2005

(65) Prior Publication Data
US 2007/0004019 A1 Jan. 4, 2007

(30) Foreign Application Priority Data
Jun. 25, 2004 (JP) ............................. 2004-188880

(51) Int. Cl.
*C12M 1/00* (2006.01)
*C12M 3/00* (2006.01)
(52) U.S. Cl. ................................................ 435/285.2
(58) Field of Classification Search .............. 435/173.6, 435/285.2
See application file for complete search history.

(56) References Cited

U.S. PATENT DOCUMENTS

| | | | |
|---|---|---|---|
| 4,971,910 A * | 11/1990 | Zimmermann | 435/285.1 |
| 5,753,477 A * | 5/1998 | Chan | 435/455 |
| 7,195,738 B2 | 3/2007 | Utsunomiya | |
| 2002/0115219 A1 * | 8/2002 | Kobayashi et al. | 435/470 |
| 2005/0220342 A1 | 10/2005 | Yamamichi | |
| 2006/0226832 A1 | 10/2006 | Ikeda et al. | |

FOREIGN PATENT DOCUMENTS

| | | |
|---|---|---|
| JP | 2642025 B2 | 5/1997 |
| JP | 11-56360 A | 3/1999 |
| JP | 2003-325176 A | 11/2003 |

OTHER PUBLICATIONS

P.J. Robinson, et al., "The Properties of Magnetic Supports in Relation to Immobilized Enzyme Reactors", Biotechnol. Bioeng., 15, 603-606, (1973).

* cited by examiner

*Primary Examiner*—Walter D Griffin
*Assistant Examiner*—Shanta G Doe
(74) *Attorney, Agent, or Firm*—Fitzpatrick, Cella, Harper & Scinto

(57) ABSTRACT

A device for introducing fine magnetic particles into a cell by applying an electric field to a reaction field where a sample solution containing cells and the fine magnetic particles are introduced, in order to form pores in the surface of the cell, and then applying a magnetic field to the reaction field to introduce the fine magnetic particles into the cell through the pore(s).

3 Claims, 4 Drawing Sheets

DEVICE AND METHOD FOR INTRODUCING PARTICLE INTO CELL AND DEVICE AND METHOD FOR COLLECTING PARTICLE FROM CELL

BACKGROUND OF THE INVENTION

1. Field of the Invention

The present invention relates to a device and a method for introducing a particle into a cell as well as a device and a method for collecting a particle out of a cell.

2. Related Background Art

P. J. Robinson et al. (Biotechnol. Bioeng., 15, 603-606 (1973)) have paid attention to the fact that the fine magnetic particles can be collected in a simple operation and reported in their research paper that fine magnetic particles may be used as an enzyme immobilization carrier for a bioreactor. In the research report, they immobilize α-chymotrypsin or β-galactosidase onto iron oxide fine particles or cellulose/iron oxide composite particles and apply such magnetic carrier particles to a complete mixed-type bioreactor. They demonstrate that such magnetic carrier particles can be easily aggregated or separated by magnetic means.

Japanese Patent No. 2642025 discloses that fine magnetic particles (for example, having an average particle size of 0.3 µm with a density of 5.2 g/cm$^3$) having a biosubstance immobilized thereon are shot into cells at a high speed (initial speed: 50 to 400 m/second) by a particle gun method, thereby introducing the biosubstance, and that the cells having the fine magnetic particles introduced therein can be selectively concentrated and separated by magnetic means. Furthermore, Japanese Patent Application Laid-Open No. 2003-325176 discloses that the efficiency of introducing particles can be improved by a particle gun method using fine composite particles having a dense magnetic substance as their cores. However, since these methods fundamentally employ a particle gun method, many cells die by mechanical shock of fine particles applied upon the cells at a high speed, with the result that the total number of cells to which fine magnetic particles are successfully introduced therein decreases. Besides this, a cell introduction step and separation step cannot be supported out continuously and a device for supporting out these steps may become large scale. These problems still remain unsolved.

On the other hand, an electroporation method is known for introducing a gene into a cell. A foreign gene is introduced into a cell by electrically stimulating the cell membrane, thereby increasing its permeability. Since the gene introduction efficiency of this method is relatively good compared to a cell fusion method as well as a particle gun method, the electroporation method has been widely used. Japanese Patent Application Laid-Open No. 11-056360 discloses a technique for applying an electric field lower in strength than a conventional electroporation method, a larger number of times, while rendering the length of an electric pulse longer. More specifically, it is disclosed that a foreign gene is introduced directly into a plant cell (without applying any pretreatment (protoplastization) to the plant cell) by applying an electric field having a strength of 50 to 500 V/cm, 5 to 25 times while controlling the length of an electric pulse at 30 to 200 msec.

As a method of collecting a target biomolecule out of a cell, methods of killing and disintegrating cells (by use of physical disintegration and autolysis of cells) are generally known. However, these methods have problems that although it is necessary to separate and purified target cells by any means in advance, the purity of a target substance is low due to the presence of contaminants.

Japanese Patent Application Laid-Open No. 2004-49105 discloses a method of selectively and exclusively separating cellular constitutional components such as DNA from target cells by use of fine magnetic particles by selectively killing and disintegrating the target cells.

In any one of these methods, cells are disintegrated to collect target biomolecules.

SUMMARY OF THE INVENTION

The present invention provides a device and a method for introducing a biomolecule into a cell, the method having a much higher introduction efficiency than conventional ones. The present invention also provides a device and a method for collecting a target biomolecule out of a cell, the method providing much less contaminants than conventional ones.

According to the present invention, there is provided a device for introducing a magnetic into a cell, comprising means for forming a pore for introducing the particle into a surface of the cell; and means for introducing the particle into the cell through the formed pore, the means for forming a pore being different from the means for introducing the particle into the cell.

According to the present invention, there is provided a device for collecting a magnetic by taking the particle out of a cell, comprising means for forming a pore for taking out the particle in a surface of the cell; and means for collecting the particle by taking the particle out of the cell through the formed pore.

According to the present invention, there is provided a method of introducing a magnetic into a cell, comprising the steps of forming a pore in membrane of the cell for introducing the particle; and introducing the particle into the cell through the pore.

According to the present invention, there is provided a method of collecting a magnetic out of a cell, comprising the steps of forming a pore in membrane of the cell for collecting the particle; and collecting the particle by taking the particle out of the cell through the pore.

According to the present invention, the following advantages are provided.

First, both an electric field and a magnetic field are applied to a reaction field where cells and fine magnetic particles are introduced. By virtue of this, the fine magnetic particles can be transferred into a cell by the magnetic field through pores formed in the cell surface by the application of the electric field.

Second, by virtue of the magnetic field applied to the reaction field, cells containing the fine magnetic particles are selectively and specifically separated from a sample solution containing fine magnetic particles and cells.

Third, by virtue of the magnetic field applied to the reaction field where a sample solution containing cells having fine magnetic particles are present, the fine magnetic particles can be moved within a cell, thereby permitting the fine magnetic particles to efficiently carry a target biomolecule.

Fourth, fine magnetic particles supporting a target biomolecule can be moved outside a cell through pores formed in the surface of a cell containing the fine magnetic particles by applying both an electric field and a magnetic field to the reaction field, with the result that the target biomolecule alone can be separated from contaminants present in the cell.

DESCRIPTION OF THE PREFERRED EMBODIMENTS

Figure 1:
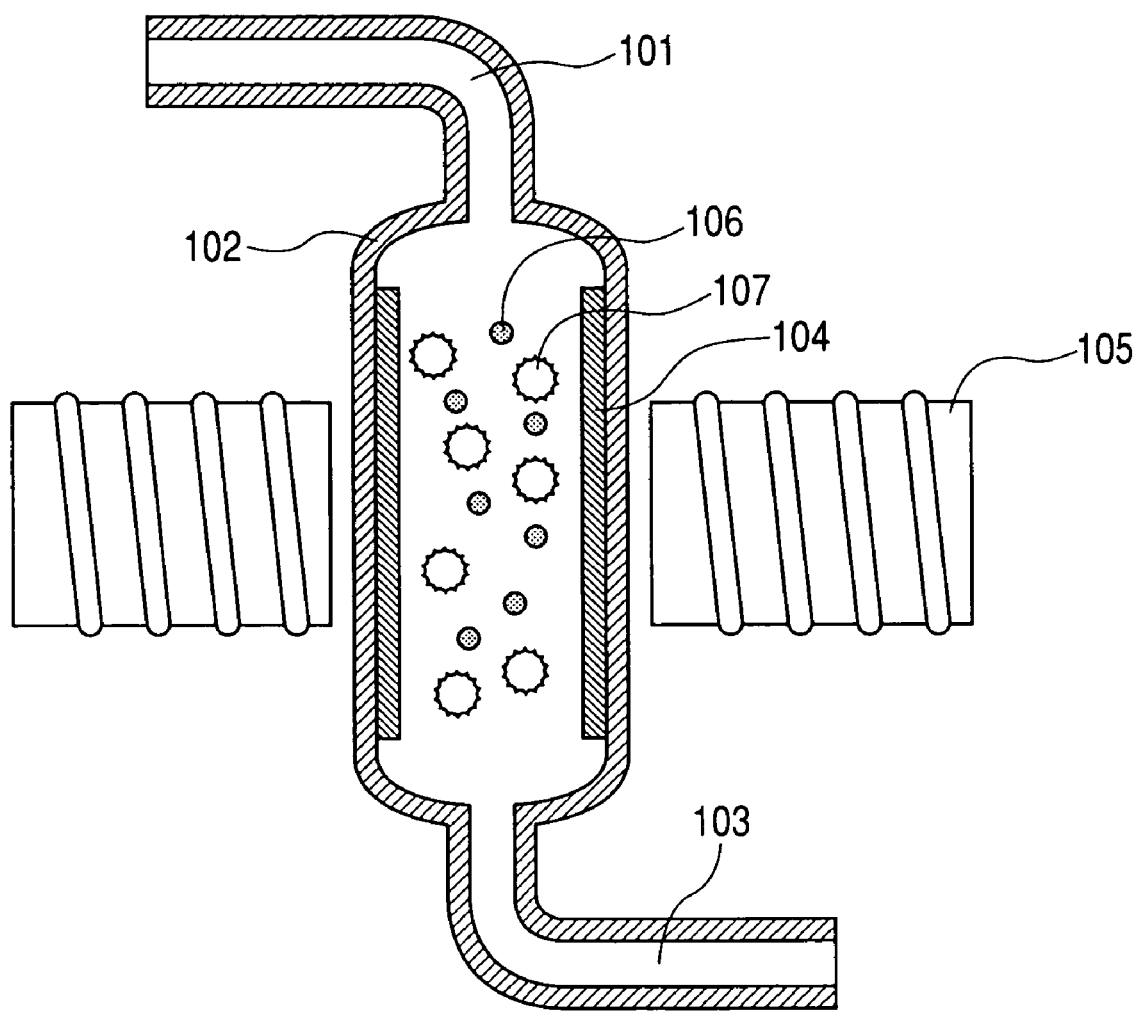
FIG. 1 is a schematic view of a device for introducing fine particles according to the present invention.

One of the basic constitutions of the present invention resides in that an electric field is applied to a reaction field where a sample solution containing cells and fine magnetic particles have been introduced, thereby forming pores in the surface of the cells, and a magnetic field is then applied to the reaction field, thereby introducing the fine magnetic particles into the cells. Furthermore, the present invention comprises selectively separating fine magnetic particles from the cells containing them by applying a magnetic field thereto, or taking fine magnetic particles out of the cells through pores formed on the cell surface without homogenizing the cells or bacteriolysis by applying both an electric field and a magnetic field, thereby collecting the fine magnetic particles. The present invention includes various devices to which these constitutions are applied and modified methods thereof.

In the present invention, both an electric field and a magnetic field are applied to a reaction field where fine magnetic particles and cells are introduced. Thus, the fine magnetic particles can be actively transferred by the magnetic field through pores formed in cell surface by the electric field. By actively transferring the fine particles into or out of cells, the efficiency of introducing a biomolecule can be improved, cells having the biomolecule introduced therein can be selectively concentrated by applying a magnetic field to collect cells and a target biomolecule alone can be collected from the cells by applying an electric field and magnetic field to collect fine particles bound to a target biomolecule from the cells.

The present invention comprises a cell separating device for selectively and exclusively separating a cell having fine magnetic particles introduced therein by applying both an electric field and a magnetic field to a reaction field containing a sample solution that contains fine magnetic particles having a biomolecule to be introduced to the cell or having a capturing substance capable of binding to a desired target substance within a cell, and cells.

In the present invention, cells may be immobilized on a carrier provided within the reaction field for efficiently transferring fine magnetic particles into the cells.

Furthermore, in the present invention, a magnetic field may be applied to a reaction field to transfer fine magnetic particles within a cell to facilitate binding of the fine magnetic particles to a desired target substance present in the cell.

In the present invention, means for guiding a sample solution containing fine magnetic particles and cells to a reaction field may be provided. Furthermore, means for discharging a washing solution for washing off contaminants, and means for collecting cells and fine particles separated may be provided.

A method of introducing fine particles into a cell according to the present invention comprises the steps of:

(1) introducing, to a reaction field, a sample solution containing fine magnetic particles having a biomolecule to be introduced into the cell or having a capturing substance capable of binding to a desired target substance in the cell, and cells;

(2) applying an electric field to the reaction field to form pores in the cell surface; and (3) applying a magnetic field to the reaction field to transfer the fine magnetic particles into the cells through pores of the cell surface formed by applying the electric field.

A method of selectively separating cells according to the present invention comprises the steps of:

(1) introducing, to a reaction field, a sample solution containing fine magnetic particles having a biomolecule to be introduced into the cell or having a capturing substance capable of binding to a desired target substance in the cell and cells;

(2) applying an electric field to the reaction field to form pores in the cell surface;

(3) applying a magnetic field to the reaction field to transfer the fine magnetic particles into the cell through pores of the cell surface formed by applying the electric field; and (4) selectively and exclusively separating cells having fine magnetic particles introduced therein, by applying a magnetic field.

A method of collecting fine particles according to the present invention comprises the steps of:

(1) introducing, to a reaction field, a sample solution containing cells that contain fine magnetic particles having a capturing substance capable of binding to a desired target substance within a cell;

(2) immobilizing the cells to a carrier;

(3) applying a magnetic field to the reaction field to facilitate the binding of the fine magnetic particles to the desired target substance within a cell, thereby moving the fine magnetic particles within the cell;

(4) applying an electric field to the reaction field to form pores in the cell surface; and (5) applying a magnetic field to the reaction field to collect the fine magnetic particles from the cell through the pores formed in the cell surface by applying the electric field, thereby transferring the fine magnetic particles from the cells.

A method of introducing fine particles into a cell and collecting the fine particles according to the present invention comprises the steps of:

(1) introducing a sample solution containing cells to a reaction field;

(2) immobilizing the cells to a carrier;

(3) applying an electric field to the reaction field to form pores in the cell surface;

(4) applying a magnetic field to the reaction field to transfer the fine magnetic particles into the cells through pores of the cell surface formed by applying the electric field;

(5) applying a magnetic field to the reaction field to facilitate the binding of the fine magnetic particles to the desired target substance within a cell, thereby moving the fine magnetic particles within the cell;

(6) applying an electric field to the reaction field to form pores in the cell surface; and (7) applying a magnetic field to the reaction field to collect the fine magnetic particles from the cell through the pores formed in the cell surface by applying the electric field, thereby transferring the fine magnetic particles from the cells.

The method of introducing fine particles, method of selectively separating cells, and method of collecting a target biomolecule according to the present invention can be suitably supported out by use of a device for introducing fine particles, a device for separating cells, and a device for target molecules, respectively.

The method of introducing fine particles, method of selectively separating cells, and method of collecting a target biomolecule according to the present invention can be suitably supported out by use of a device for introducing fine particles, a device for separating cells, and a device for collecting target molecules, respectively.

In the devices for introducing fine particles, separating cells and collecting target molecules discharging means can be provided for discharging contaminants, fine particles remaining unintroduced and a washing solution. Furthermore, in these devices, it is preferable that a pair of electrodes serving as means for applying an electric field are provided so as to face each other at least with the reaction field interposed between them. Furthermore, the means for applying an electric field is preferably an electric pulse in order to prevent disintegration of cells and suppress stress due to pore formation from being applied to cells. Note that the means for applying an electric field can be appropriately selected depending upon the length of electric pulse and application times; and the electric field strength may be selected depending upon the types of cells and the types of sample solutions. In a device according to the present invention, it is preferable that the means for applying a magnetic field can generate a magnetic field by electromagnetic induction upon supplying power, since generation of the magnetic field and magnetic field strength can be easily controlled. As means for applying a magnetic field, at least two magnetic poles are preferably arranged so as to face each other with the reaction field interposed between them, since the direction of the magnetic field can be easily controlled.

In the present invention, the fine magnetic particles may be any type of magnetic substance; they may be a substance, for example, having superparamagnetic, paramagnetic, or ferromagnetic properties. Examples of materials for fine magnetic particles include metals, metal oxides, non-metal/metal composites, ceramic composites, and organic magnetic substances containing any one of the aforementioned materials and a naturally occurring or a synthetic organic compound, and composites thereof.

The diameters of the fine magnetic particles may fall at largest within the range from about one fourth of the size of a target cell to the size of fine particles. The fine magnetic particles having an average diameter of 1 nm to 50 μm may be used. More preferably, to transfer the fine magnetic particles under application of a magnetic field, particles have an average diameter of 5 nm or more; however, the maximum particle size varies depending upon the size of a cell.

As the carrier for use in adsorbing cells containing fine magnetic particles, any material may be used as long as it has a structure of passing fine magnetic particles and cells. Examples of such a material include glass fiber, ceramic, silicon, nitrocellulose membrane, and PVDF membrane. It is preferable that the carrier is substance having a structure through which fine magnetic particles, solution and cells can pass or a porous material. The pore size of the porous material may be appropriately selected depending upon the sizes of cells and fine particles; however, they are preferably 500 μm or less where the fine particles and cells may come closer to each other in advance, in consideration of cell size.

The carrier may have any type of surface as long as it can adsorb cells having a biological substance to be introduced or cells containing fine magnetic particles which has the biological substance entrapped. For example, fibronectine, polylysine, RGD, collagen, laminin, an antibody against a cell surface antigen, an amino group, a carboxyl group, an epoxy group, an aldehyde group, or a hydroxyl group may be present on the surface. The carrier may have any type of surface depending upon the purpose.

In the present invention, any form of the reaction field may be used; however, a capillary and a micro channel are preferable in view of efficient application of both an electric field and a magnetic field and reduction of a sample solution in volume.

The fine magnetic particles may have any type of surface as long as the surface can bind to a biomolecule to be introduced or a desired cellular target substance by means of physical adsorption, chemical bonding, electrostatic bonding, hydrophobic bonding or intermolecular force. The surface of the fine magnetic particles may be formed of at least one material selected from the group consisting of metals, metal oxides, inorganic semiconductors, organic semiconductors, glasses, ceramics, naturally occurring polymers (containing natural macromolecules), synthetic polymers and plastics, or a composite thereof.

A biomolecule selected from the group consisting of nucleic acids, proteins, sugar chains, lipids and complexes thereof may be used as the biomolecule of the invention. More specifically, the present invention can be applied to any molecule containing at least one type of biomolecule selected from the group consisting of DNA, RNA, aptamer, gene, chromosome, mitochondria, virus, antigen, antibody, lectin, hapten, hormone, receptor, enzyme, peptide, sphingolipid, and sphingosugar.

EXAMPLES

The present invention will be described in more detail by way of Examples, below, which should not be construed as limiting the present invention.

Example 1

(Device for Introducing Fine Particles)

FIG. 1 shows a schematic structure of a device for introducing fine particles according to the present invention. In the figure, a sample solution containing fine magnetic particles 106 and cells 107 is introduced into a reaction field 102 from an inlet channel 101. The reaction field 102 is a region at which the fine magnetic particles 106 are introduced into the cells 107. At least one pair of electrodes 104 are arranged so as to face each other with the reaction field 102 interposed between them, and furthermore at least one electromagnet 105 is arranged. In this example, a pair of electromagnets are provided so as to face each other with the reaction field interposed between them. Furthermore, a discharge channel 103 is arranged for discharging cells 107 having no fine magnetic particles 106 introduced therein, and fine magnetic particles from the reaction field 102, and collecting them. The pair of electrodes 104 and coils of the electromagnets 105 are connected to a pulse generating power source.

It goes without saying that a plurality of pairs of electrodes 104 can be arranged.

Note that a permanent magnet can be used as the electromagnet 105. However, an electromagnet is preferable since on/off drive of a magnetic field and the strength thereof can be controlled by means of on/off operation of current and voltage application.

First, a sample solution containing the fine magnetic particles 106 and the cells 107 is pored into the reaction field 102 through the inlet channel 101. The sample solution containing the fine magnetic particles 106 and the cells 107 may be a buffer solution, water and a softening agent for cell membrane. An open/close valve (not shown) is provided between the reaction field 102 and the discharge channel 103. The valve is preferably closed when the sample solution containing the fine magnetic particles 106 and the cells 107 is introduced into the reaction field 102.

Note that a stirring device such as a propeller may be provided for stirring the sample solution containing the fine magnetic particles 106 and the cells 107 in the reaction field.

Then, a pulse voltage is applied to the pair of electrodes arranged so as to sandwich the reaction field. When the pulse voltage is applied such that the potential difference across the cells becomes about 1 V or more, transient pores are formed in the membrane surface of a cell. This phenomenon is called electroporation. More specifically, when a voltage is applied, ions migrate within a cell so as to cancel out the potential difference between the portions of the cell membrane facing both electrodes, with the result that a potential difference is generated across the cell membrane. Such a potential difference induces electrostatic discharge, which damages the cell membrane. The electromagnets 105 arranged so as to sandwich the reaction field therebetween are driven almost simultaneously with the application of an electric field. In this manner, the fine magnetic particles 106 present in the reaction field can be introduced into the cells through electroporates.

Since the electroporates thus formed will close within several milli-seconds, a magnetic field must be generated by the electromagnets within the time to efficiently transfer the magnet fine particles. This operation may be supported out optimally by controlling pulse-voltage application times, voltage and pattern of pulse for electroporation, or optionally controlling on/off operation of the electromagnet and the strength of the magnetic field.

Generally, the magnetic field strength is increased in parallel to a current value to be applied to the coil of the electromagnet. Since the coil has a constant ohmic value, the current flowing through the coil increases in proportion to the voltage to be applied to the coil. Therefore, the following explanation will be made by use of the voltage to be applied to the coil.

Figure 2:
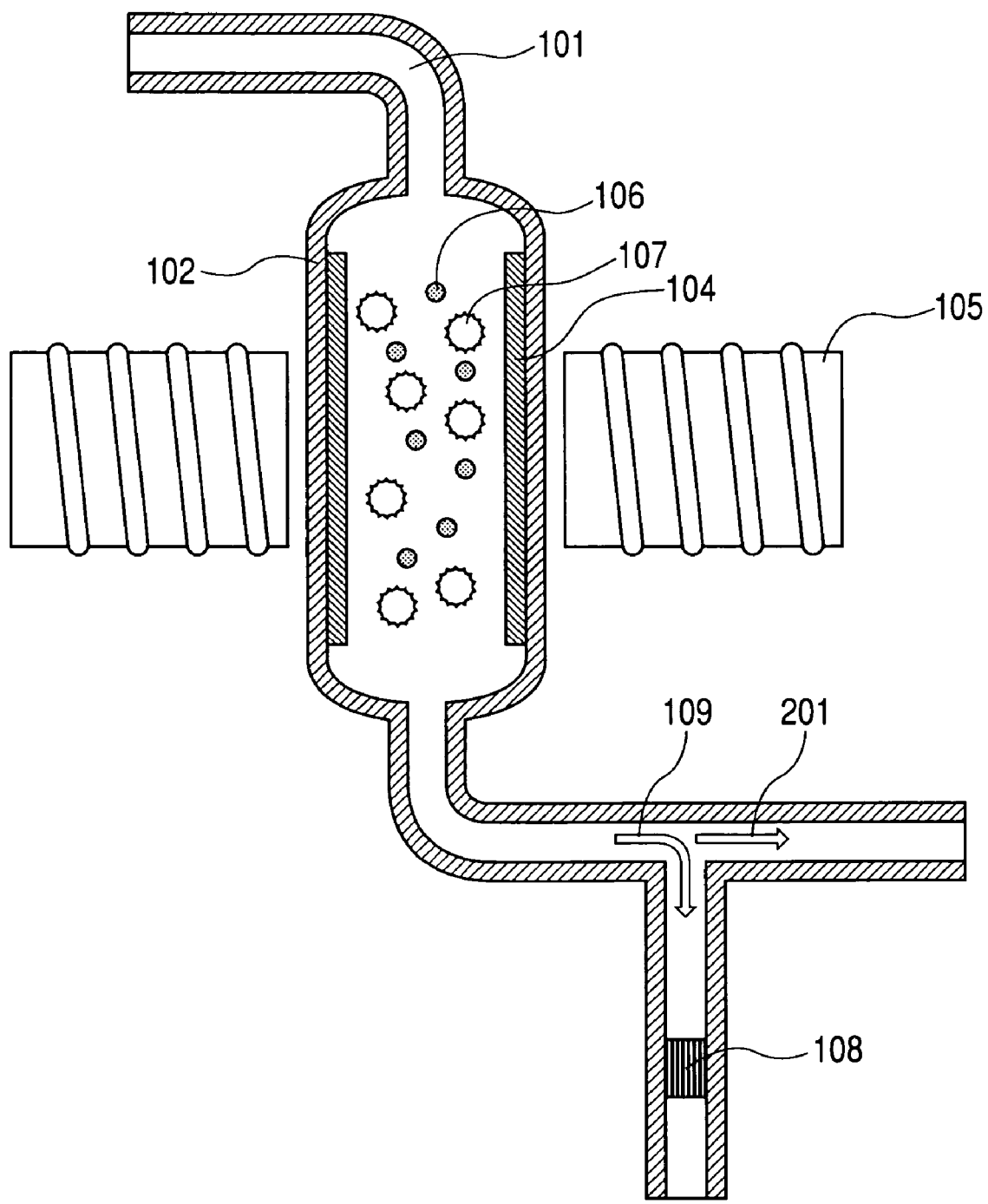
FIG. 2 is a schematic view of a device for separating cells according to the present invention.
Figure 3:
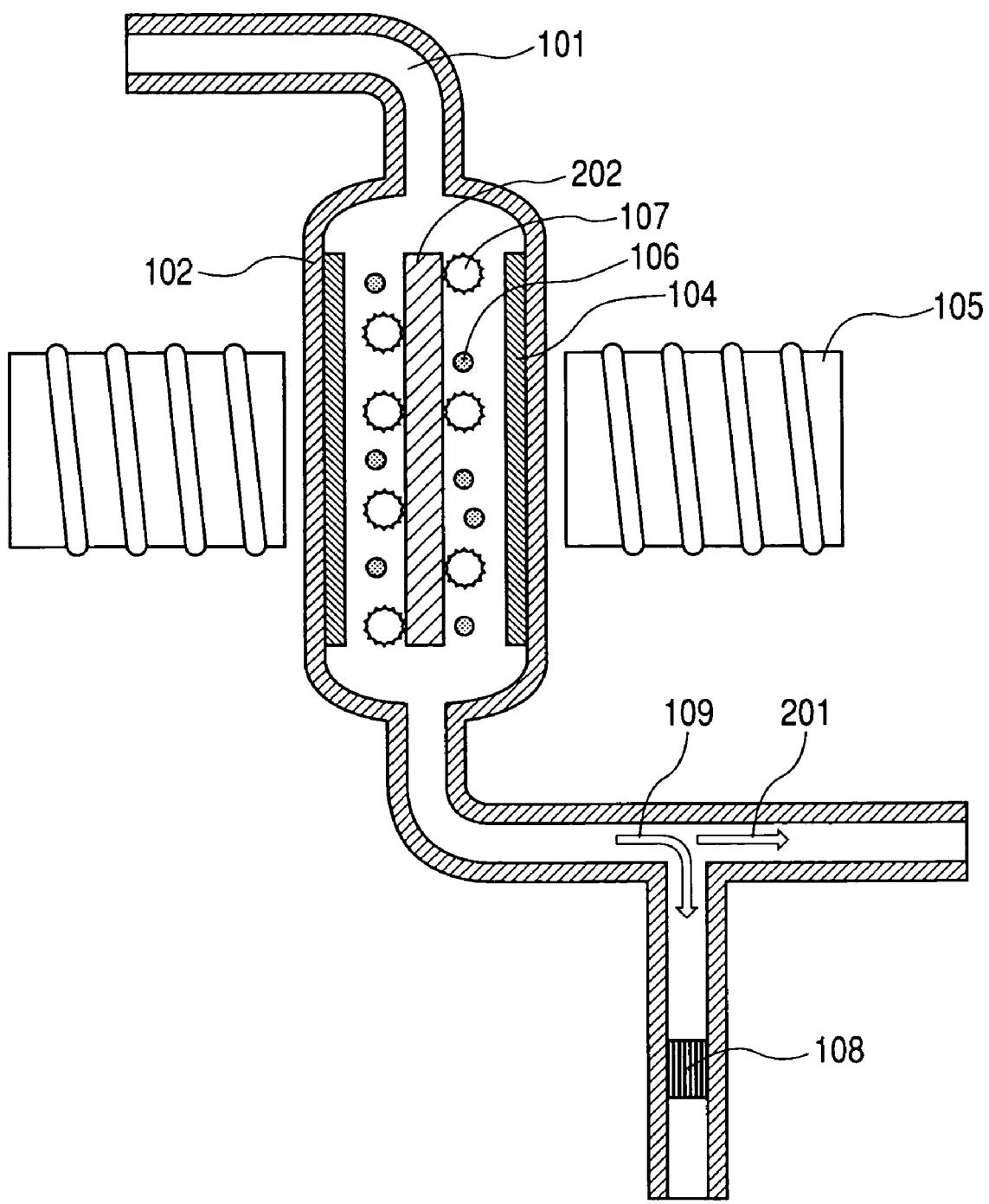
FIG. 3 is a schematic view of a device for collecting fine particles according to the present invention.

In the reaction field, at least one of electromagnets must be arranged. In FIGS. 1 to 3, a pair of electromagnets are arranged so as to face each other. To introduce fine magnetic particles into a cell through electroporates formed in the cell membrane surface, individual fine magnetic particles preferably move at random near the electroporates.

In the manner as described in this Example, fine magnetic particles can be efficiently introduced into a cell. At present, several types of fine magnetic particles are commercially available and the surface of the particles is modified in order to bind to a biomolecule. Various types of biomolecules may be efficiently introduced into a cell by use of such biomolecule binding fine magnetic particles in accordance with the present invention.

Note that, in this Example, a capillary having an inner diameter of 1 mm is used as the reaction field 102. Pulse voltages shown in FIG. 4 are applied to the electrodes 104 and the coils of the electromagnet 105. More specifically, a pulse voltage of 1.6 kV having a pulse width of 20 μsec. is applied to the electrode 104, whereas a pulse voltage having a pulse width of 50 μsec. capable of generating a magnetic field of 150 m$^3$/kg is applied to the electromagnet.

As a result, it is possible to obtain a potential difference of about 1 V or more across the cell.

In the case where a plurality of electromagnets 105 are arranged, a voltage may be applied such that the electromagnets 105 have the same polarity or a different polarity from each other. In FIG. 4, explanation is made by taking a case where a single electromagnet is arranged as an example, for the brevity's sake. The voltage to be applied to a coil and the strength of the magnetic field are in proportional relationship and regulates a speed of transferring fine magnetic particles. By applying the pulse voltage as mentioned above to the coil of the electromagnet, the fine magnetic particles can be efficiently introduced into a cell.

Figure 4A:
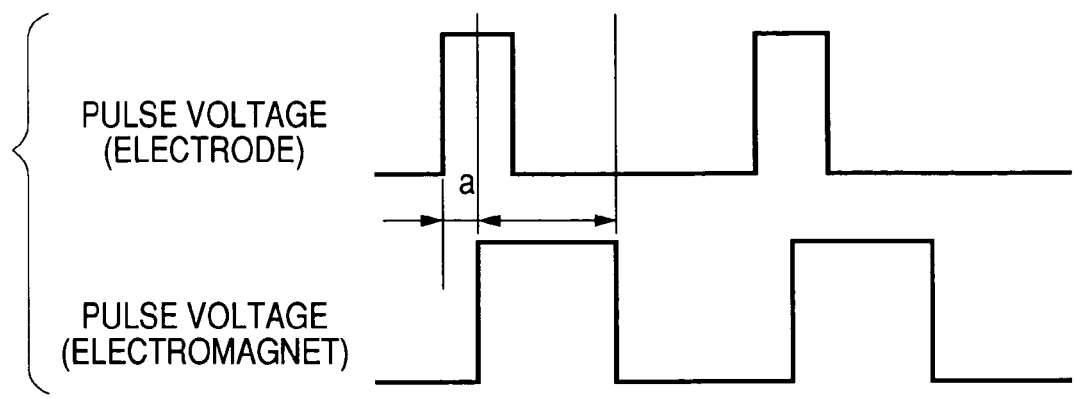
FIGS. 4A and 4B are timing charts illustrating pulse voltage for forming both an electric field and a magnetic field.
Figure 4B:
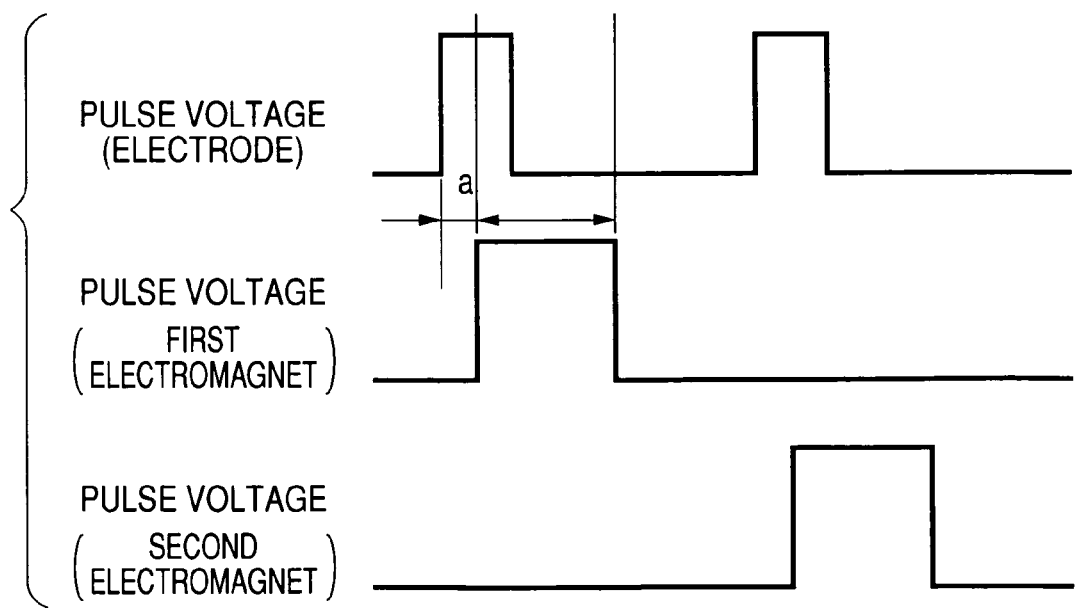

In FIG. 4A, at the moment when electroporates are formed by applying a pulse voltage to the electrode 104 and thus a cell is ready to receive fine magnetic particles, the fine magnetic particles must be transferred by applying a pulse voltage to the electromagnet 105. In this Example, immediately after a time period (a) during which electroporates are formed by applying a pulse voltage to the electrode 104, a pulse voltage is applied to a coil to transfer and introduce the fine magnetic particles 106 into a cell. At this time, when the magnetic field is applied in a single direction, the fine magnetic particles 106 are attracted toward the electromagnet 105. Therefore, as shown in FIG. 4B, it is preferable that the electromagnets 105 are arranged so as to sandwich the reaction field 102 and the magnetic field is alternately changed. Thus, attraction of the fine magnetic particles 106 toward the electrode 105 can be avoided.

In the state where electroporates formed in the surface of the cell 107 are closed, it is not necessary to transfer the fine magnetic particles 106. Therefore, after the passage of time (b) during which the electroporates of the cell 107 close by the application of no voltage (0V) to the electrode 104, the voltage to be applied to the electromagnet 105 is set at 0V.

The arrangement of the pair of electrodes, the pulse current to be applied to the electrodes, the arrangement of the electromagnet 105, and the pulse current to be applied to the electromagnet 105 are not limited to this Example. It goes without saying that optimal conditions may be appropriately selected since the time period during which electroporates are opened varies depending upon the types of cells.

Example 2

(A Device for Separating Cells)

FIG. 2 shows a schematic structure of a device for separating cells according to the present invention. In this Example, a branched discharge channel (branched into two parts) is used in place of the discharge channel 103 of the fine particle introducing device according to Example 1. The flow channel 109 is a discharge channel, whereas the flow channel 201 is a collection channel. An ultrafiltration filter 108 is disposed in the flow channel 109.

A sample solution containing fine magnetic particles 106 and cells 107 is introduced into the reaction field 102 and then transient electroporates are formed in the surface membrane of the cells 107 to introduce fine magnetic particles 106 into a cell through the electroporates, in the same manner as in Example 1.

Subsequently, to collect magnetic substances near one of the coils of the electromagnet 105, the one of the coils of the electromagnet 105 is driven by applying a voltage of direct current, thereby aggregating cells containing fine magnetic particles and the fine magnetic particles 106, near the one of the coils of the electromagnet 105. While maintaining this state, a washing solution is poured through the inlet flow channel 101 to wash fine magnetic particles 106 adsorbed or un-adsorbed onto the reaction field 102 and cells having no fine magnetic particles 106 introduced therein, and then guided toward the collection channel 201.

After completion of washing, the electromagnet 105 is turned off and the cells containing fine magnetic particles are guided toward the collection channel 109 with an appropriate buffer solution. In this manner, the cells containing fine magnetic particles (hereinafter simply referred to as "fine magnetic particle containing cells") are separated from fine magnetic particles and collected.

In the cell introducing device shown in FIG. 1, after contaminants, that is, cells having no fine magnetic particles introduced therein, and the washing solution are discharged through the discharge channel 103, the cells having fine magnetic particles introduced therein can be collected through the discharge channel 103. However, in this Example, free fine magnetic particles can be separated from the magnetic fine particle containing cells aggregated by means of the electromagnet, by the ultrafiltration filter 108 provided in the discharge channel 109. After the separation, the fine magnetic particle containing cells alone can be selectively collected with high purity through the collection channel 201.

The efficiency of introducing fine magnetic particles can be calculated based on the number of cells having no fine magnetic particles introduced therein and previously collected through the collection channel 201, and the number of fine magnetic particles containing cells selectively collected.

As in this Example, fine magnetic particle containing cells can be readily collected by branching the discharge channel into a discharge channel having an ultrafiltration filter provided therein and a collection channel.

At present, various types of fine magnetic particles are commercially available and the surface of the fine magnetic particles is modified so as to bind to biomolecules. If the present invention is supported out by use of such fine magnetic particles binding to a biomolecule, various biomolecules can be efficiently introduced into a cell and the resultant cells can be efficiently collected. In addition, it is possible to separate off free fine magnetic particles, which may prevent a biological operation to be performed after the present invention is applied.

Example 3

(Device for Collecting Fine Particles)

FIG. 3 shows a schematic structure of a device for collecting fine particles according to the present invention. In this Example, a structure 202 having a surface capable of supporting cells is placed within the reaction field 102 of the cell separating device according to Example 2. The structure 202 can adsorb cells onto the surface and has pores through which cells, a sample solution, and fine magnetic particles can pass.

This Example can be supported out by injecting fine magnetic particle containing cells through the inlet channel 101. However, it is desirable that this Example is supported out subsequently after fine magnetic particles are introduced into the cells in accordance with Example 1. The operation how to carry out the Example will be described below.

In the same manner as in Example 1, first, a sample solution containing fine magnetic particles 106 and cells 107 is poured through the inlet channel 101 and introduced into the reaction field 102. The sample solution containing cells 107 may be a buffer solution, water and a cell-softening agent. The fine magnetic particles have a surface capable of capturing a biomolecule within a cell. To describe more specifically, if oligo dT is present on the surface, poly A RNA (nucleic acid) within a cell can be specifically captured. The cells injected can be adsorbed onto the structure 202 arranged in the reaction field. If an antibody against a cell surface antigen is immobilized on the surface of the structure 202, the structure 202 can adsorb and immobilize the cells by capturing the cell surface antigen.

Next, a pulse voltage is applied to a pair of electrodes arranged so as to sandwich the reaction field to form transient electroporates in the cell membrane surface. Simultaneously upon the application of the electric field, the coils of the electromagnet 105 arranged so as to sandwich the reaction field are driven to introduce the fine magnetic particles 106 present in the reaction field into a cell through the electroporates.

Subsequently, the coils of the electromagnet 105 arranged so as to sandwich the reaction field are only driven to move fine magnetic particles within a cell. Then, one of the coils of the electromagnet 105 arranged so as to sandwich the reaction field is driven to localize the fine magnetic particles within the cell near the cell wall in the proximity of the driven coil. According to this Example, fine magnet particles are allowed to be in contact with various types of biomolecules such as poly A RNA present in a cell more frequently. Furthermore, fine magnetic particles can be localized near the cell wall so as to facilitate collection of the fine magnetic particles from the cell. The migration route of fine magnetic particles can be controlled by regulating on/off of the electromagnet.

Next, a pulse voltage is applied to a pair of electrodes arranged so as to sandwich the reaction field 102 to form transient electroporates in the cell membrane surface. Simultaneously upon the application of the electric field, the coils of the electrode 105 arranged so as to sandwich the reaction field 102 are driven to transfer fine magnetic particles 106 present in the reaction field from the cells through the electroporates.

Subsequently, to collect magnetic substances near one of the coils of the electromagnet 105, the one of the coils of the electromagnet 105 is driven, thereby aggregating the fine magnetic particles 106 transferred out of the cells. While maintaining this state, a washing solution is poured through the inlet channel 101 to wash the reaction field 102 and guided toward the discharge channel 109. After washing, the one of the coils of the electromagnet 105 is turned off and the fine magnetic particles are guided toward the collection channel 201 with an appropriate buffer solution. In this way, the fine magnetic particles can be collected.

According to this Example, since it may not be necessary to disintegrate cells, it is possible to specifically collect a target biological substance with a significantly small amount of contaminants, compared to a conventional method for collecting a biomolecule out of a cell.

Furthermore, a biomolecule having an interaction with a target biomolecule can be specifically collected by use of fine magnetic particles capable of capturing the target biomolecule according to this Example.

This application claims priority from Japanese Patent Application No. 2004-188880 filed Jun. 25, 2004, which is hereby incorporated by reference herein.

What is claimed is:

1. A method of collecting a magnetic particle out of a cell using a device for introducing the particle into the cell comprising means for forming a pore in the surface of the cell to introduce the particle into the cell, means for introducing the particle into the cell through the formed pore, and means for collecting the particle by taking the particle out of the cell through a pore formed by the means for forming a pore, wherein the means for forming a pore is different from the means for introducing the particle into the cell, the method comprising the steps of:

forming a pore in the membrane of the cell to collect the particle; and collecting the particle by taking the particle out of the cell through the pore.

2. The method according to claim 1, further comprising the steps of:
(1) introducing, to a reaction field, a sample solution containing cells that contain fine magnetic particles having a capturing substance capable of binding to a desired target substance within a cell;
(2) immobilizing the cells to a carrier;
(3) applying a magnetic field to the reaction field to facilitate the binding of the fine magnetic particles to the desired target substance within a cell, thereby moving the fine magnetic particles within the cell;
(4) applying an electric field to the reaction field to form pores in the cell surface; and
(5) applying a magnetic field to the reaction field to collect the fine magnetic particles from the cell through the pores formed in the cell surface by applying the electric field, thereby transferring the fine magnetic particles from the cells.

3. A method of introducing fine particles into a cell and collecting the fine particles, comprising the steps of:
(1) introducing a sample solution containing cells to a reaction field;
(2) immobilizing the cells to a carrier;
(3) applying an electric field to the reaction field to form pores in the cell surface;
(4) applying a magnetic field to the reaction field to transfer the fine magnetic particles into the cells through pores of the cell surface formed by applying the electric field;
(5) applying a magnetic field to the reaction field to facilitate the binding of the fine magnetic particles to the desired target substance within a cell, thereby moving the fine magnetic particles within the cell;
(6) applying an electric field to the reaction field to form pores in the cell surface; and
(7) applying a magnetic field to the reaction field to collect the fine magnetic particles from the cell trough the pores formed in the cell surface by applying the electric field, thereby transferring the fine magnetic particles from the cells.

* * * * *